US011565107B2

(12) United States Patent
Broderick et al.

(10) Patent No.: US 11,565,107 B2
(45) Date of Patent: Jan. 31, 2023

(54) TOLERABLE AND MINIMALLY INVASIVE SKIN ELECTROPORATION DEVICE

(75) Inventors: Kate Broderick, San Diego, CA (US); Jay McCoy, San Diego, CA (US); Stephen V. Kemmerrer, San Diego, CA (US); Feng Lin, San Diego, CA (US); Rune Kjeken, Oslo (NO)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 705 days.

(21) Appl. No.: 13/581,702

(22) PCT Filed: Mar. 1, 2011

(86) PCT No.: PCT/US2011/026701
§ 371 (c)(1),
(2), (4) Date: Oct. 5, 2012

(87) PCT Pub. No.: WO2011/109406
PCT Pub. Date: Sep. 9, 2011

(65) Prior Publication Data
US 2013/0066296 A1    Mar. 14, 2013

Related U.S. Application Data

(60) Provisional application No. 61/309,422, filed on Mar. 1, 2010.

(51) Int. Cl.
*A61N 1/32* (2006.01)
*A61N 1/05* (2006.01)
(Continued)

(52) U.S. Cl.
CPC .............. *A61N 1/327* (2013.01); *A61K 39/12* (2013.01); *A61K 39/145* (2013.01);
(Continued)

(58) Field of Classification Search
CPC .. A61N 1/0452; A61N 1/0476; A61N 1/0502; A61N 1/0504; A61N 1/306;
(Continued)

(56) References Cited

U.S. PATENT DOCUMENTS 3,994,287 A * 11/1976 Turp ................. A61B 17/3498
604/167.06
5,968,006 A    10/1999 Hofmann et al.
(Continued)

FOREIGN PATENT DOCUMENTS

WO    0044438    8/2000
WO    0113989    3/2001
(Continued)

OTHER PUBLICATIONS

Ashara, Kalpesh Chhotalal and Shah, Ketan Vinodlal. Elementary of animal model for percutaneous and ocular penetration. Asian Pacific Journal of Tropical Disease. 2016. 6(12) 1007-1010. (Year: 2016).*

(Continued)

*Primary Examiner* — Jason E Flick
(74) *Attorney, Agent, or Firm* — BakerHostetler

(57) ABSTRACT

A novel electroporation device for the delivery of vaccines that is both effective in generating a protective immune response and tolerable delivery to a subject (or near painless); and also methods of using same device to vaccinate a subject against a variety of infectious diseases and types of cancer in a near painless.

20 Claims, 12 Drawing Sheets

Battery powered Minimally Invasive EP Device with detachable array
(for sterilization)

"a" shows external view. "b" shows inside view (including batteries).

(51) Int. Cl.
*A61K 39/145* (2006.01)
*A61K 39/12* (2006.01)
*A61K 39/00* (2006.01)

(52) U.S. Cl.
CPC ........ *A61N 1/0502* (2013.01); *A61K 2039/53* (2013.01); *A61K 2039/54* (2013.01); *C12N 2760/16134* (2013.01)

(58) Field of Classification Search
CPC . A61N 1/327; A61N 1/18; A61N 1/32; A61N 1/00; A61N 1/04; A61N 1/05; A16M 5/3286; A16M 2205/195; A61K 2039/53; A61K 2039/54; A61K 39/12; A61K 39/145; A61P 31/16; C12N 2760/16134
See application file for complete search history.

(56) References Cited

U.S. PATENT DOCUMENTS

| | | | | |
|---|---|---|---|---|
| 6,241,701 B1* | 6/2001 | Hofmann | ............... | A61N 1/325 604/21 |
| 6,277,116 B1* | 8/2001 | Utely | ............... | A61B 18/14 606/41 |
| 6,603,998 B1* | 8/2003 | King | ............... | A61P 43/00 604/20 |
| 7,054,685 B2 | 5/2006 | Dimmer et al. | | |
| 7,922,709 B2 | 4/2011 | Zhang et al. | | |
| 2002/0010412 A1* | 1/2002 | Eppstein | ............ | A61B 5/14514 604/10 |
| 2002/0193833 A1* | 12/2002 | Dimmer | ............... | A61N 1/325 607/3 |
| 2005/0119605 A1* | 6/2005 | Sohn | ............... | A61N 1/0424 604/21 |
| 2005/0215941 A1 | 9/2005 | Bernard et al. | | |
| 2006/0036210 A1 | 2/2006 | Zhang et al. | | |
| 2006/0084938 A1* | 4/2006 | Zhang | ............... | A61N 1/327 604/501 |
| 2007/0016268 A1 | 1/2007 | Carter et al. | | |
| 2007/0021712 A1 | 1/2007 | Bernard et al. | | |
| 2010/0160712 A1* | 6/2010 | Burnett | ............. | A61N 1/36007 600/13 |

FOREIGN PATENT DOCUMENTS

| | | |
|---|---|---|
| WO | 2008/094664 | 8/2008 |
| WO | 2007/095140 | 2/2009 |

OTHER PUBLICATIONS

Wilke et al., "Silicon microneedle electrode array with temperature monitoring for electroporation" Sensors and Actuators A 123-124 (2005), pp. 319-325.

Rabussay "Applicator and Electrode Design for In Vivo DNA Delivery by Electroporation" Electroporation Protocols: Preclinical and Clinical Gene Medicine, Methods in Molecular Biology, vol. 423, Chapters, 2008, pp. 35-59.

* cited by examiner

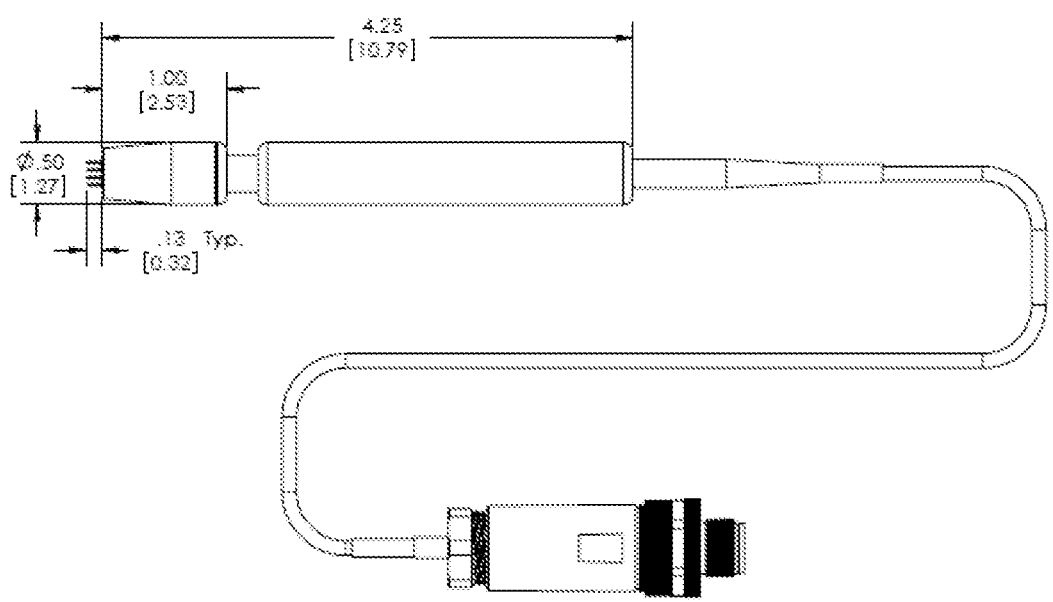
Figure 1 – Assembly of Minimally Invasive EP Device

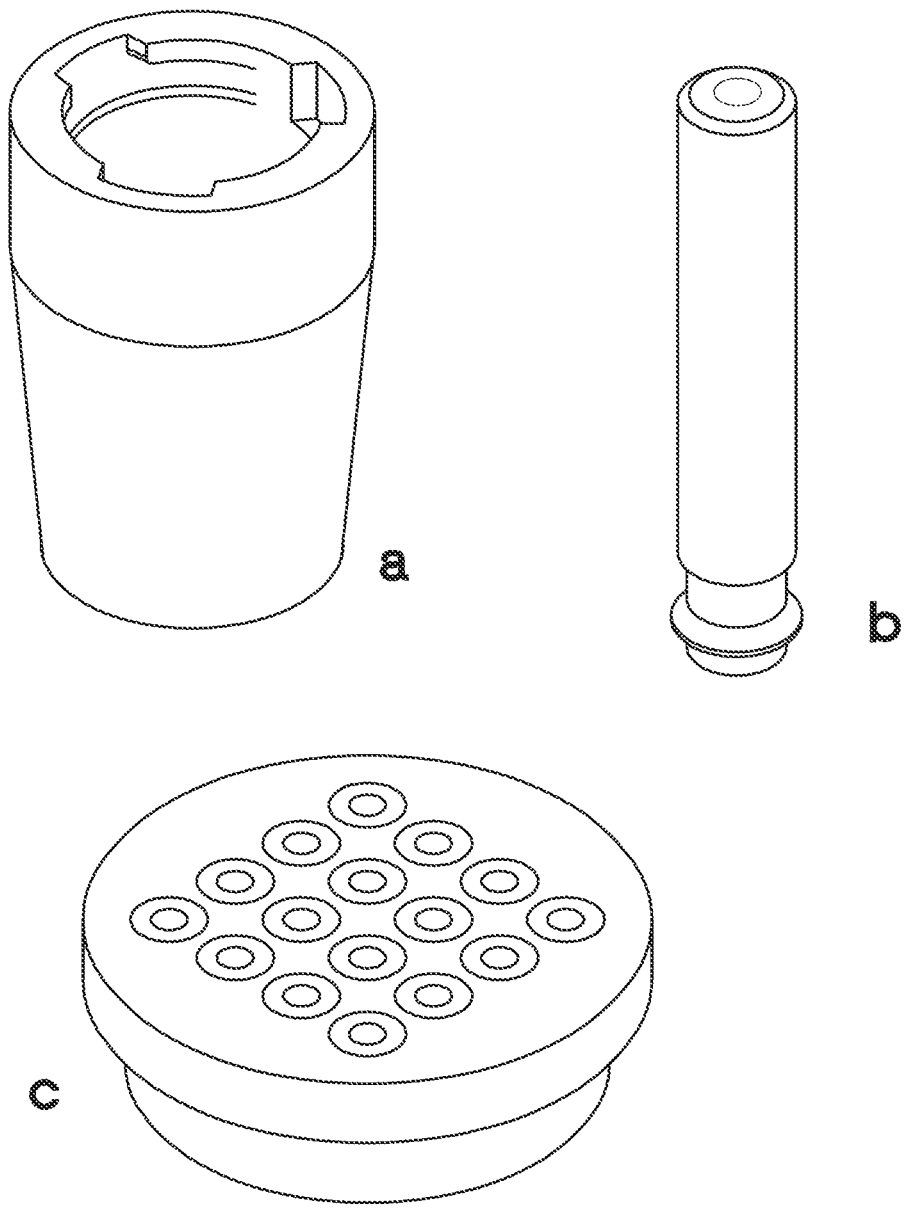
Figure 2 – Components of MIED. "a" shows disposable sterile array housing, "b" shows the durable housing and "c" shows the electrode housing within the disposable array (2a).

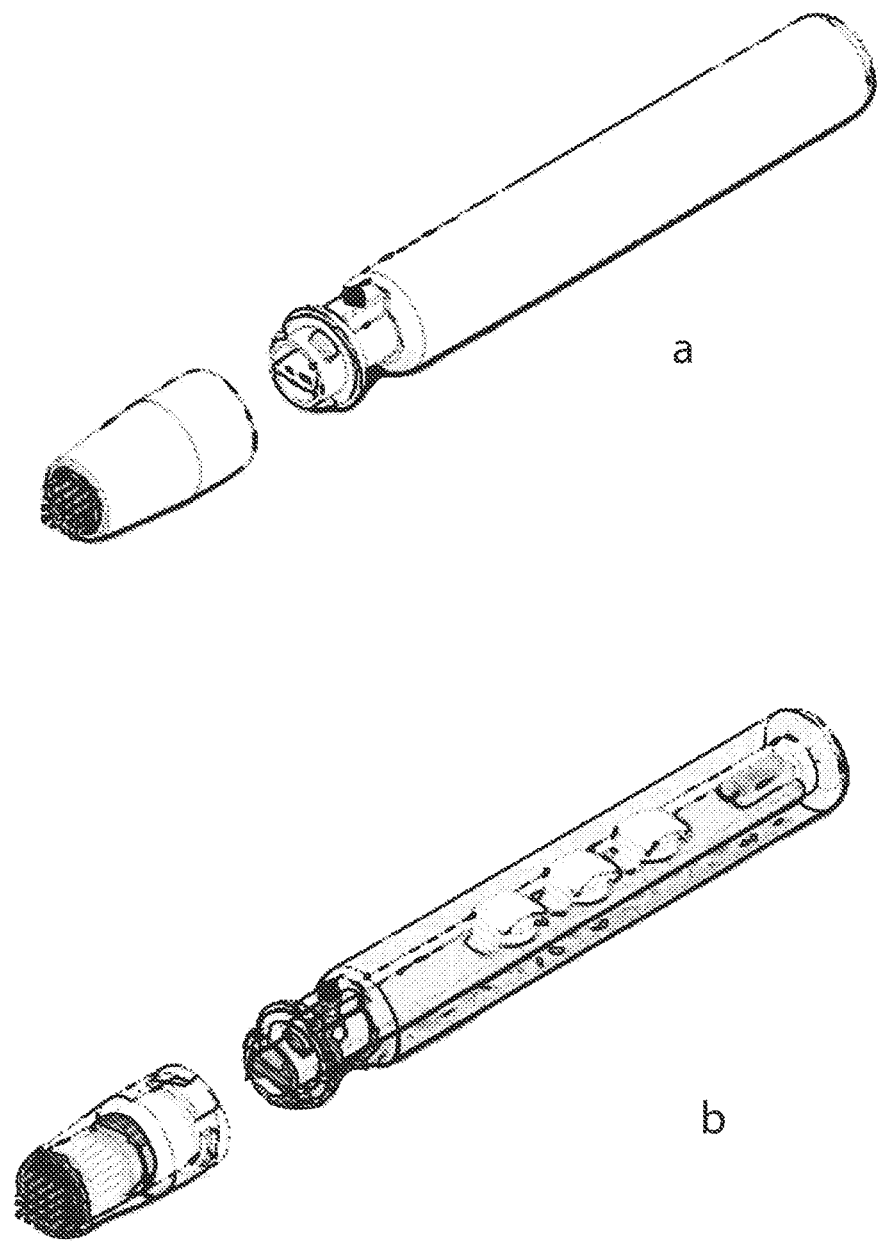
Figure 3 – Battery powered Minimally Invasive EP Device with detachable array (for sterilization)
"a" shows external view. "b" shows inside view (including batteries).

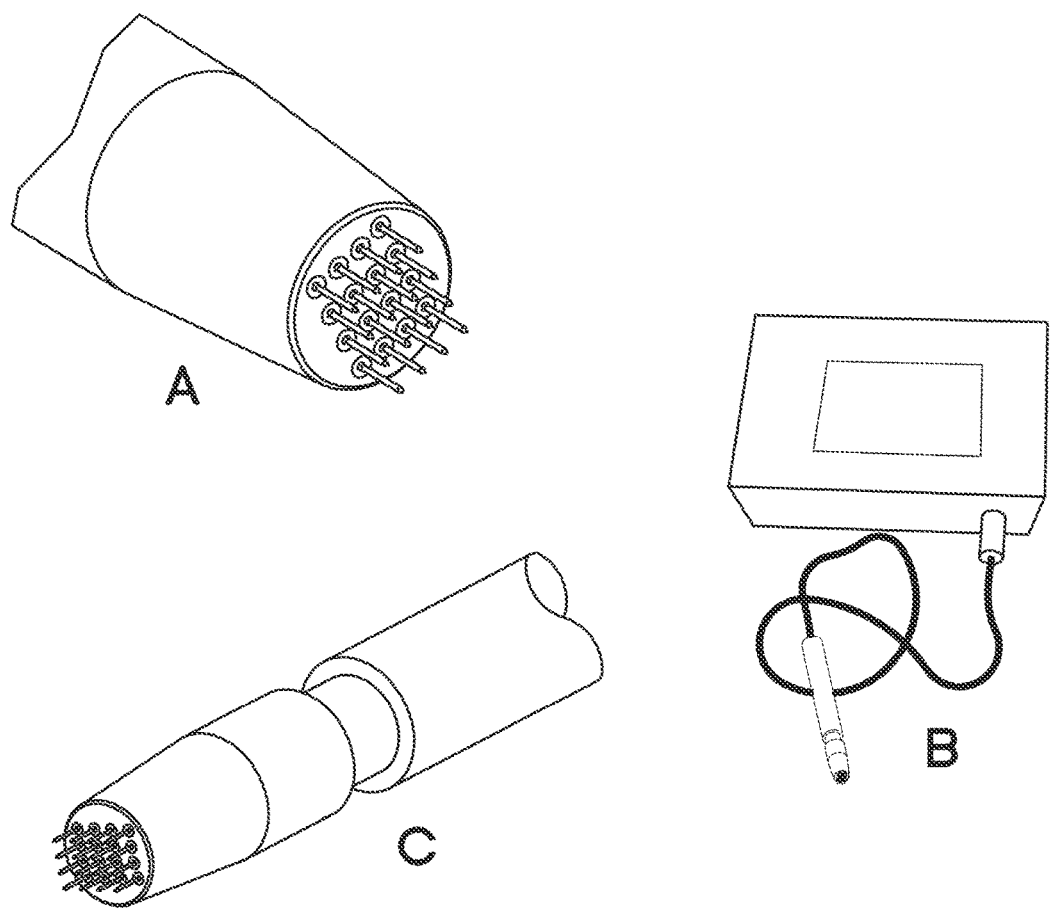

Figure 4 Minimally-invasive electroporation device (A) CAD drawing of a prototype minimally- invasive device consisting of trocar gold-coated needle electrodes at 1.5 mm spacing in a 4 x 4 array pattern. (B) The array is attached to the handle of the device and connected directly into the pulse generator, in this case, the Elgen 1000. EP can be triggered either through activation of a foot pedal or a trigger button on the screen (C) The built functioning prototype.

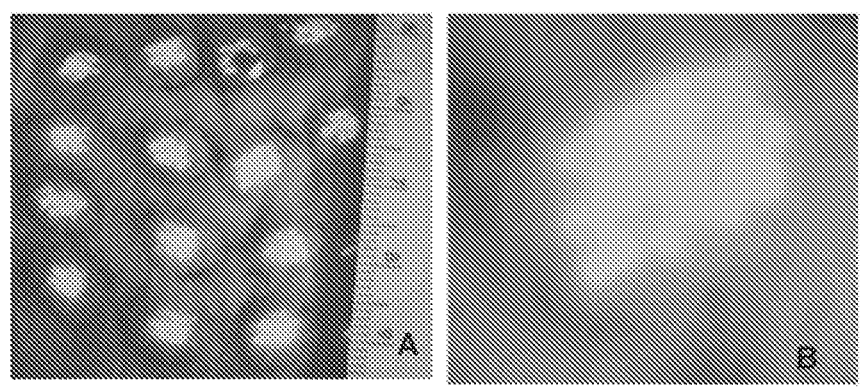

Figure 5 - Electroporation using a minimally-invasive device results in robust reporter gene transfection Green fluorescent protein (GFP) expression after ID plasmid administration followed by electroporation (EP) with the minimally-invasive device in guinea pig skin. (A) Plasmids were delivered at multiple sites (14) and the pattern compared in size to the array. (B) Magnified example of a single treatment site showing the transfection occurring at the contact point with the electrodes.

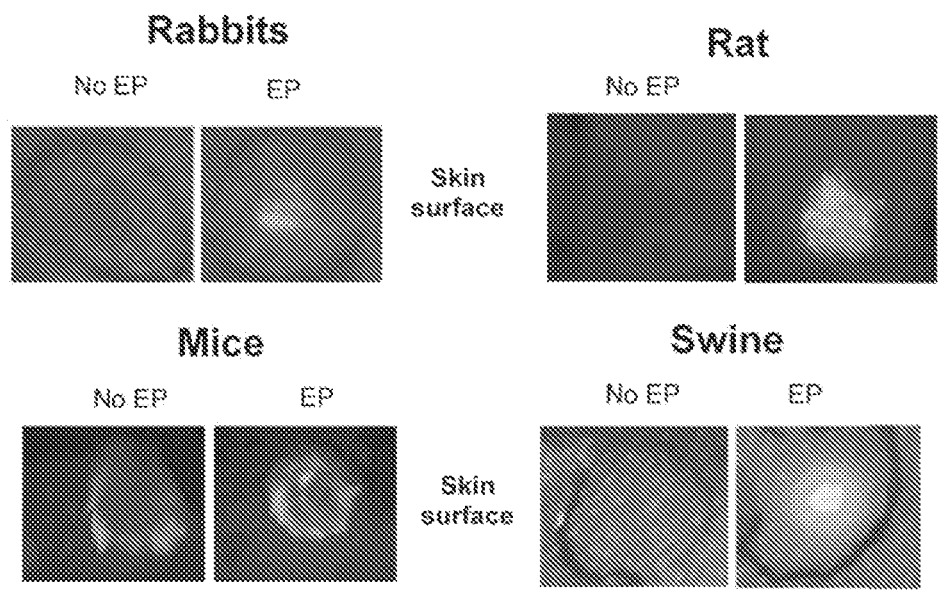

Figure 6 - Minimally-invasive electroporation results in positive transfection in a wide spectrum of species
Green fluorescent protein (GFP) expression after ID plasmid administration with or without electroporation (EP) with the minimally-invasive device in rabbit, mouse and pig skin. Panels show the skin tissue after animal sacrifice 3 days following treatment. The panels show either skin which was injected with GFP plasmid alone or immediately followed with EP. Only the topside (skin surface) views are shown. The underside (underlying muscle) of skin showed no positive transfection.

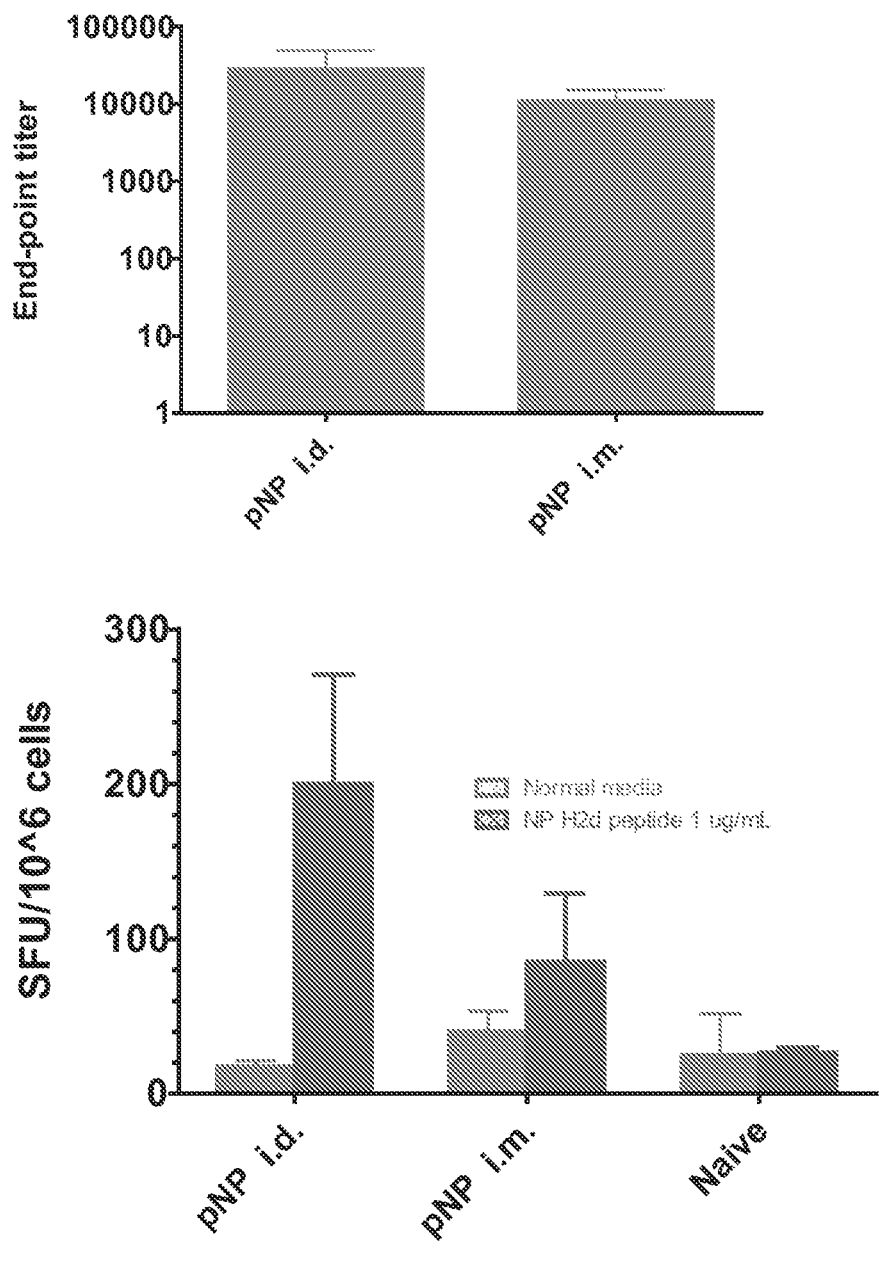

Figure 7A

Humoral and cellular immunogenicity results in protection from influenza challenge in mice Electroporation with the minimally-invasive device results in robust antibody and cellular responses which confers protection on mice following a lethal influenza challenge. (7A) Mice were immunized with plasmid (3 ug) expressing the antigenic NP protein from influenza using either an i.d. route (minimally-invasive device) or i.m. (Elgen Twininjector). Antibody titers and antigen specific T-cell ELISPot assays were measured.

Figure 7B

Humoral and cellular immunogenicity results in protection from influenza challenge in mice Electroporation with the minimally-invasive device results in robust antibody and cellular responses which confers protection on mice following a lethal influenza challenge. (7B) Immunized animals were protected against for morbidity and mortality when challenged with VN/1203/04 (H5N1) strain of influenza

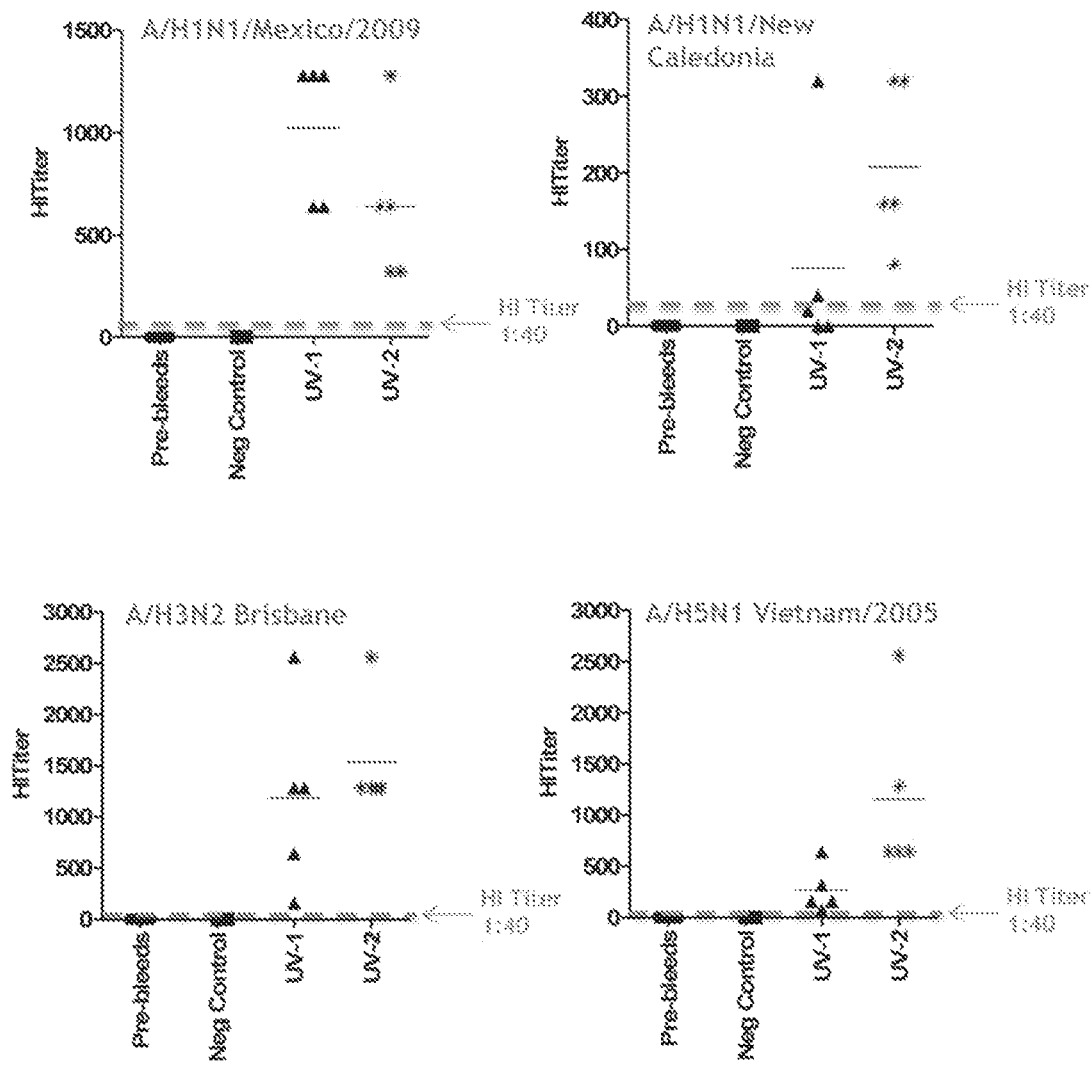

Figure 8 - Humoral immunogenicity results in protective HAI titers in guinea pigs HAI titers from individual macaques 2 weeks following the third immunization against H1N1 (Mexico/2009 and New Caledonia), H3N2 (Brisbane) and H5N1 (Vietnam/2005) strains. Animals were immunized with previously described SynCon influenza plasmid vaccines via either the i.d. route (minimally-invasive) or i.m. route (Elgen Twininjector).

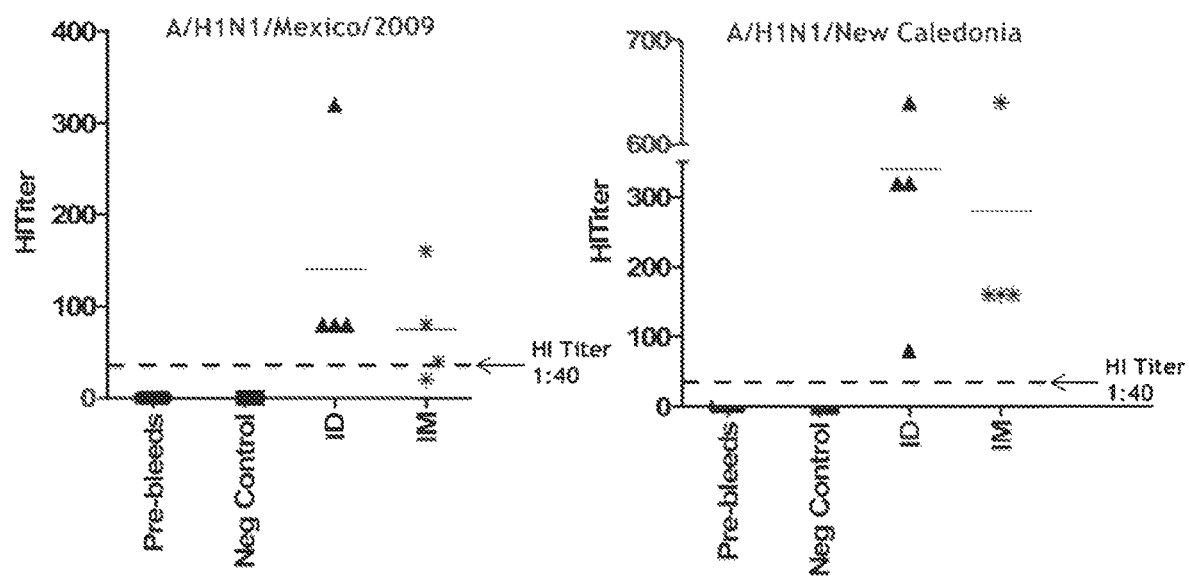

Figure 9 - Humoral immunogenicity results in protective HAI titers in nonhuman primates
HAI titers from individual macaques 2 weeks following the second immunization against two H1N1 strains (Mexico/2009 and New Caledonia). Animals were immunized with previously published SynCon influenza plasmid vaccines via either the i.d. route (minimally-invasive) or i.m. route (Elgen Twininjector).

TOLERABLE AND MINIMALLY INVASIVE SKIN ELECTROPORATION DEVICE

CROSS-REFERENCE TO RELATED APPLICATIONS SECTION

This application is a 371 National stage entry of International Application No. PCT/US2011/026701, filed Mar. 1, 2011, and claims the benefit of U.S. Provisional Application No. 61/309,422, filed Mar. 1, 2010, the contents of which are incorporated herein by reference.

This work was supported in part by US Army grant W23RYX-8141-N604: #08023003.

FIELD OF THE INVENTION

The present invention relates to, among other things, electroporation devices and their use for facilitating the introduction of biomolecules into cells of skin tissue in a mammal

BACKGROUND

The magnitude of the immune response to a DNA vaccine can often times depend on three main criteria—the optimized vector design, the use of a suitable adjuvant and the successful delivery and subsequent expression of the plasmid in the target tissue. In vivo electroporation has proved to be particularly effective in efficiently delivering DNA immunogens to the muscle and the skin and indeed several devices have entered into human clinical trials.

Drug delivery to dermal tissue (intradermal, ID) is an attractive method in a clinical setting for a number of reasons. The skin is the largest organ of the human body, the most accessible, most easily monitored, as well as being highly immuno-competent. However, the impervious, barrier function of the skin has been a major obstacle to efficient trans-dermal drug delivery.

Human skin extends to approximately 2 m$^2$ in area and is around 2.5 mm thick on average, making it the largest organ of the human body. Conventionally, the skin has two broad tissue types, the epidermis and the dermis. The epidermis is a continually keratinizing stratified epithelium. The outer most layer of skin is the stratum corneum (SC) and acts as the primary barrier function for skin. The SC is a 15-30 cell thick layer of non-viable but biochemically active corneocytes. The other three strata of the epidermis (*S. granulosum, S. spinosum, S. basale*) all contain ketatinocytes at different stages of differentiation as well as the immune Langerhans cells and dermal dendritic cells.

Both physical and chemical methods for trans-dermal drug delivery and gene delivery have been detailed by groups worldwide. Iontophoresis, lipid delivery and gene gun are such examples. One other physical method to temporarily increase skin permeability is electroporation. Electroporation involves the application of brief electrical pulses that result in the creation of aqueous pathways within the lipid bi-layer membranes of mammalian cells. This allows the passage of large molecules, including DNA, over the cell membrane which would otherwise be less permeable. As such, electroporation increases the uptake, as well as the extent to which drugs and DNA are delivered to their target tissue. For electroporation to cause the formation of pores, a threshold energy needs to be achieved and the movement produced by the electrophoretic effect depends upon both the electric field and the pulse length.

In the case of DNA vaccines, electroporation has been shown to quantitatively enhance immune responses, increase the breadth of those immune responses as well as improve the efficiency of dose. The many advantages of skin delivery, most notably presence of a variety of immune relevant cells, easy clinical accessibility as an immunization target organ, and the minimal depth of delivery (minimally invasive) is attractive; however, questions persist as to the ability of achieving high transfection rates and subsequently robust immune responses.

The delivery of naked DNA through a standard intramuscular (IM) injection is notoriously inefficient outside of rodent models. This has lead to an inability to achieve robust immune responses in large mammals and humans. Several strategies have been developed to enhance the expression of DNA-based vaccines, such as codon-optimization, RNA optimization, leader sequence addition and the development of optimized consensus sequences.

Despite the improvements in vector design and use of molecular adjuvants, there still remains a need for an efficient method of administrating DNA vaccines that results in high level expression of the plasmid in the desired cell type of the desired tissue, most commonly, muscle, tumor or skin. Furthermore, there remains a need for an electroporation device and method of delivering vaccines that is both effective in generating a protective immune response and tolerable (or near painless).

SUMMARY OF INVENTION

In an aspect of the invention, there are electroporation devices capable of delivering to a subject a tolerable electrical potential to layers of epidermal tissue between stratum corneum and basal layers that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers via the electrodes an electrical potential of about 0.1 volts to about 50 volts to the epidermal tissue; and the electrodes have a tip on the distal end that is blunt with a sharp point allowing the electrode to penetrate layers of epidermis tissue between stratum corneum and basal layers, and delivers the electrical potential from the voltage generator to the epidermis tissue.

In another aspect of the invention, there are electroporation devices capable of delivering to a subject a tolerable electrical potential to epidermal tissue that results in electroporation of cells in said epidermal tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers via the electrodes an electrical potential of about 0.1 volts to about 50 volts to the epidermal tissue; and the electrodes are adapted to penetrate the epidermal tissue at depths of 0.1 mm or less.

In another aspect of the invention, there are electroporation devices capable of delivering to a subject a tolerable electrical potential to epidermal tissue that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers to the array an electrical field of about 0.1 to about 50 volts; and wherein the electrodes deliver a tolerable electrical potential to the cells of the epidermal tissue that are near painless as measured by a visual analog scale.

In another aspect of the invention, three are electroporation devices capable of delivering to a subject a tolerable electrical potential to epidermal tissue that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers to the array an electrical field of about 0.1 to about 50 volts; and wherein the electrodes deliver a tolerable electrical potential to the cells of the epidermal tissue as evidence by minimal tissue damage in said cells.

In another aspect of the invention, there are tolerable methods of delivering a biomolecule to cells of epidermal tissue of a subject by electroporation assisted delivery using the electroporation devices described herein, comprising: administering the biomolecule to the cells; contacting the electrodes to the epidermal tissue so that the electrodes penetrate through the stratum corneum and reside in layers above the basal layers; and delivering a tolerable electrical potential from the voltage generator to the cells of the epidermal layer via the electrodes.

BRIEF DESCRIPTION OF THE DRAWINGS

The numerous objects and advantages of the present invention may be better understood by those skilled in the art by reference to the accompanying figures, in which:

FIG. 1 displays an equal 15 mm length muscle electrode array.

FIG. 2 displays an equal 4 mm length muscle electrode array.

FIG. 3 displays one embodiment of the present invention: a 4×4 electrode array wherein the IM electrode are the corners of 4×4 array, while the remaining 12 electrodes can be either 3 mm invasive dermal or the pointy surface dermal style.

FIG. 4 displays pictures three-dimensional drawings of an embodiment of the MIED.

FIG. 5 shows the ID injection being passed by the invasive IM electrode portion of one of the embodiment of the invention.

FIG. 6 shows the addition of the IM injection (in addition to that shown in FIG. 7) and demonstrates the additional transfection by the longer invasive electrodes, which locally treat the IM injection, FIGS. 7A and 7B display graphs showing immunogenicity results in protection from influenza challenge in mice.

FIG. 8 displays a drawing showing the dual depth electroporation delivery in comparison to ID or IM alone.

FIG. 9 displays graphs that depict antibody responses from vaccinated guinea pigs using one of the preferred embodiments.

DETAILED DESCRIPTION OF THE INVENTION

Figure 10:
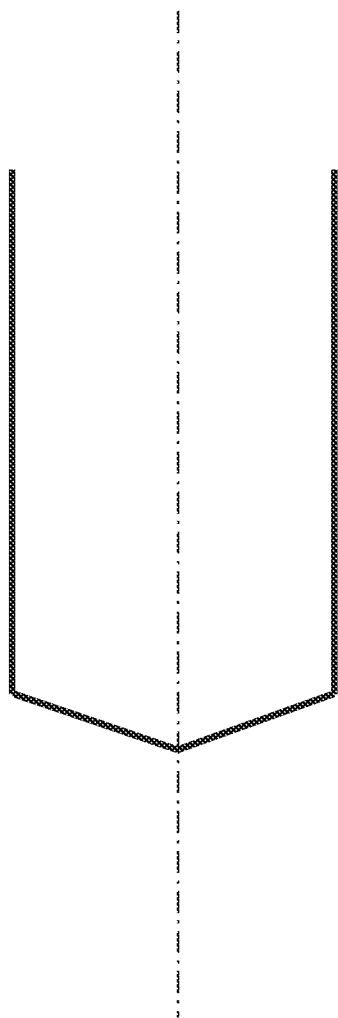
FIG. 10 displays an electroporation needle with a distal end that is blunt with a sharp point.
Figure 11:
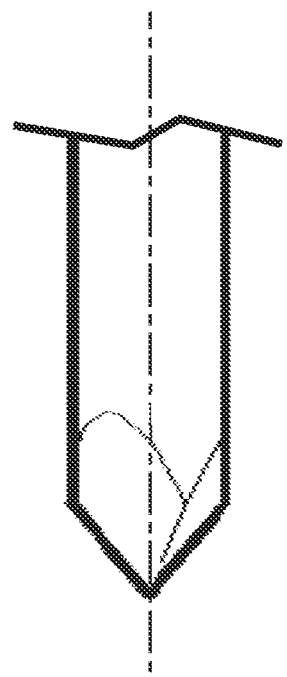
FIG. 11 displays a needle electrode having a distal end that defines a trocar tip having a plurality of planar surfaces that extend distally to a sharp point.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller. The current amperage values described to be delivered by the devices herein are preferably constant current amperage values.

The term "constant voltage" is used herein to define a voltage or electric potential that is received or experienced by a tissue, or cells defining said tissue, over the duration of an electrical pulse delivered to same tissue. The electrical pulse is delivered from the electroporation devices described herein. This voltage remains at a constant voltage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output so the voltage in same tissue remains constant throughout the electrical pulse (on the order of microseconds), and from pulse to pulse. In some embodiments, the feedback element comprises a controller. The voltage values described to be delivered by the devices herein are preferably constant voltage values.

The term "feedback" or "current feedback" is used interchangeably and means the active response of the provided skin EP devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the skin EP device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The term "biomolecule" as used herein refers to nucleic acid sequences, proteins, lipids, microbubbles (e.g. drug-loaded vesicles), and pharmaceuticals. Preferably the biomolecule is a vaccine, and more preferably the biomolecule is a DNA vaccine, and even more preferably a DNA plasmid vaccine.

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "minimally invasive" as used herein refers to a limited penetration by the needle electrodes of the provided electroporation device, and can include noninvasive electrodes (or nonpenetrating needles). Preferably, the penetration is to a degree that penetrates through stratum corneum, and preferably enters into outer most living tissue layer, the stratum granulosum, but does not penetrate the basal layer. Penetration depth not to exceed 0.1 mm, and preferably depths ranging from about 0.010 mm to about 0.040 mm to break through stratum corneum. Preferably, this is accomplished using an electrode that has a trocar end ground to provide a sharp point that allows penetration through the stratum corneum but avoid deep penetration.

The term "tolerable" or "near painless," is used herein interchangeably, and when referring to electroporation, means a substantially lower level of pain associated with electroporation than typical with available electroporation devices. More specifically, the tolerable (or near painless) electroporation is the result of combination of using the MIED described herein, avoiding electroporation of muscle, along with delivering low electrical fields to the epidermal layers between the stratum corneum and the basal layers. Preferably the electrical fields will be comprised of low voltage levels, i.e., for example from 0.01V to 70 V, and preferably from 1 V to 15 V. When measured using a visual analog scale or VAS, subjects experiencing the MIED electroporation according to the methods provided herein experience pain levels that are within 20% (of the full scale) from their painless or pain free score, for example, within 2 points, with 0-10 full scale, and preferably within 10% from their painless score.

In an aspect of the invention, there are electroporation devices capable of delivering to a subject a tolerable electrical potential to layers of epidermal tissue between stratum corneum and basal layers that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers via the electrodes an electrical potential of about 0.1 volts to about 50 volts to the epidermal tissue; and the electrodes have a tip on the distal end that is blunt with a sharp point allowing the electrode to penetrate layers of epidermis tissue between stratum corneum and basal layers, and delivers the electrical potential from the voltage generator to the epidermis tissue. In some instances, the electrodes have a tip on the distal end that is generally blunt but has a sharp point, or in other words a sharp point followed by shallow or blunt angles. For example, the electrode can have a distal end that is a trocar tip of grinds 10° off axis, to nearly perpendicular to the needle axis.

In another aspect of the invention, there are electroporation devices capable of delivering to a subject a tolerable electrical potential to epidermal tissue that results in electroporation of cells in said epidermal tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers via the electrodes an electrical potential of about 0.1 volts to about 50 volts to the epidermal tissue; and the electrodes are adapted to penetrate the epidermal tissue at depths of 0.1 mm or less.

In another aspect of the invention, there are electroporation devices capable of delivering to a subject a tolerable electrical potential to epidermal tissue that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers to the array an electrical field of about 0.1 to about 50 volts; and wherein the electrodes deliver a tolerable electrical potential to the cells of the epidermal tissue that are near painless as measured by a visual analog scale.

In another aspect of the invention, there are electroporation devices capable of delivering to a subject a tolerable electrical potential to epidermal tissue that results in electroporation of cells in said tissue comprising: a voltage generator; and an array having a plurality of electrodes in electrical communication with the voltage generator. Each one of the plurality of electrodes are spaced apart from each adjacent electrode at a distance of about 0.5 mm to about 2.5 mm; the voltage generator delivers to the array an electrical field of about 0.1 to about 50 volts; and wherein the electrodes deliver a tolerable electrical potential to the cells of the epidermal tissue as evidence by minimal tissue damage in said cells.

In some embodiments, the devices have electrodes that are adapted to penetrate the epidermal tissue at depths of 0.1 mm or less, and preferably at depths of from about 0.01 mm to about 0.04 mm. Preferably, the electrodes are spaced apart from each adjacent electrode at a distance of about 1.5 mm. Also, preferably, the voltage generator delivers to the epidermis tissue an electrical potential of about 1 volt to about 15 volts, and more preferably about 15 volts.

In some embodiments, the devices deliver the tolerable electrical potential the electrical potential for a duration ranging from about 5 msec to about 250 msec, duration ranges and times in between.

In some embodiments, the devices deliver a tolerable electrical potential that generates a pain assessment by said subject that is near painless as measured by a visual analog scale. VAS is a 100-mm—long horizontal line on which 0 mm indicated no pain and 100 mm indicated worst pain. Near painless is a score using the VAS methodology that produces a mean score of about <20 mm (within 95% confidence interval), and preferably <10 mm (within 95% confidence interval).

In some embodiments, the devices deliver a tolerable electrical potential that is an electrical potential that results in minimal tissue damage in said cells of the subject, and preferably no visible tissue damage per histopathology analysis of the tissue. Histological analysis can be utilized to assess visual damage.

Histological Analysis Demonstrates Transfection in the Upper Layers of the Epidermis Histopathological analysis was made of guinea pig skin tissue. Each panel showed tissue which has been electroporated by MIED. All slides have been stained with hematoxylin and eosin as well as viewed under fluorescent microscope (×20 objective) to visualize GFP positively. The histopathology of skin tissue after animal sacrifice 3 days after treatment was shown: the analysis revealed no associated tissue damage following electroporation with the minimally-invasive device. In other words, the histopathology analysis of the tissue with electroporation showed similar to tissue without electroporation.

In another aspect of the invention, there are tolerable methods of delivering a biomolecule to cells of epidermal tissue of a subject by electroporation assisted delivery using the electroporation devices described herein, comprising: administering the biomolecule to the cells; contacting the electrodes to the epidermal tissue so that the electrodes penetrate through the stratum corneum and reside in layers above the basal layers; and delivering a tolerable electrical potential from the voltage generator to the cells of the epidermal layer via the electrodes.

In some embodiments, the methods comprise manipulating the electrodes to penetrate the epidermal tissue at depths of 0.1 mm or less, and preferably at depths of from about 0.01 mm to about 0.04 mm. The array can be manually adjusted back and forth (or wiggled) at the injection site to ensure good contact and result in tip of the electrodes breaking through the stratum corneum layer. Preferably, the delivering step comprises delivering a tolerable electrical potential that generates a pain assessment by said subject that is near painless as measured by a visual analog scale. Also, preferably, the delivering step comprises delivering a tolerable electrical potential that results in minimal tissue damage in said cells of the subject. The delivering step preferably delivers an electrical potential of about 0.1 volts to about 15 volts to the cells.

In some embodiments, the methods include the delivering step that comprises delivering an electrical potential for a duration of about 5 msec to about 250 msec, and duration ranges and numbers therebetween, and preferably 100 msec.

General Electroporation Devices

There are provided electroporation device generators or controllers that can deliver a pulse of electrical energy to a epidermal tissue between the stratum corneum and basal layers at low electric fields to cause tolerable electroporation. Preferably, electroporation will occur at the stratum granulosum layer primarily or exclusively. The devices deliver the pulse of energy through the provided MIED via the needle electrodes that are able to penetrate through the stratum corneum.

In some embodiments, the responsiveness of the present MIED, which preferably maintains a constant current in the treated tissue, is accomplished through a feedback mechanism in the skin EP device, which prevents heating of a tissue, and reduces tissue damage, pain and contributes to the overall success of the skin electroporation technology provided. In some embodiments, the MIED can further comprise of a controller; a waveform generator in electronic communication with the controller; a waveform logger in electronic communication with the controller; and a battery electrically connected to the waveform generator. The controller can receive an input from the user, instruct the waveform generator to deliver the pulse of energy to the desired tissue according to the input, and communicate data to the waveform logger according to the pulse of energy delivered; and wherein the battery sends an electrical charge to the waveform generator, the battery being a lithium ion, nickel metal hydride, lead acid, or nickel cadmium battery. Preferably, the MIED (FIG. 3) is portable. The portable device can be operated via a battery pack, and suitable for mass vaccination for therapeutic or vaccination purposes.

The MIED can be a combination of the provided electrode array and applicator along with a variety of electric field generating (or electric pulse generating) components, or generators. In some examples, the generators can be chosen from one of the known electroporation devices, including but not limited to the following: the electroporation devices described in U.S. Pat. No. 7,245,963, entitled, "Constant Current Electrode Assembly for Electroporation," and U.S. Pat. Nos. 5,273,525, 6,110,161, 6,261,281, 6,958,060, and 6,939,862, among others. In more preferred examples, the generators are those used with the CELLECTRA® EP device and Elgen EP device (both from Inovio Pharmaceuticals, Inc., Blue Bell, Pa.). The aforementioned patent references are hereby incorporated by reference in their entirety.

Electroporation Needles

A variety of known electroporation needles capable of delivering an electrical charge can be incorporated into the MIED. The electroporation needles are minimally invasive, which includes noninvasive needles. Preferably, the needles are sharp, e.g., some instances use a trocar grind, so that they can penetrate through the stratum corneum and reach the stratum granulosum. The trocar end can be ground to leave a sharp point that allows penetration through the stratum corneum but avoid deep penetration. In some examples, the electrodes have a tip on the distal end that is generally blunt but has a sharp point, or in other words a sharp point followed by shallow or blunt angles, e.g., the electrode can have a distal end that is a trocar tip of grinds 10° off axis, to nearly perpendicular to the needle axis Arrays A multitude of needle array formations known can be used with the current MIED. These needle array formations contemplated include any number of electrodes, any geometric pattern of electrodes in a general planar arrangement. Preferably, the electrodes are arranged evenly distributed over the electrode array (or over the base or substrate to which the electrodes are attached). More preferably, the needle electrodes are arranged in a square like arrangements with each adjacent needle electrode spaced apart in approximately the same distance (except for the electrodes on the edge of the square).

In some embodiments the array is comprised of at least three needles equally spaced apart in a triangle pattern, at least four needles equally spaced apart in a circular pattern, or needles arranged in a 2×2, 3×3, 4×4, 5×5, or greater, square pattern. Alternatively, the pattern can be rectangular or rhomboid. Preferably, the needle electrodes are arranged in a 4×4 needle array arrangement. An example of the 4×4 needle array is shown in FIG. 1. FIG. 2 shows an example of the MIED housing, array housing and electrode housing. Each needle electrode can be spaced apart from each adjacent needle electrode at a distance of 150 mm or less, from 100 mm to 1 mm, from 50 mm to 1 mm, from 40 mm to 1 mm, from 30 mm to 1 mm, from 20 mm to 1 mm, from 10 mm to 1 mm, from 5 mm to 1 mm, from 5 mm to 2 mm, from 5 mm to 2 mm, and preferably 2 mm, and more preferably 1.5 mm.

Electrical Pulses (Delivered Electric Potential)

The provided devices operate at lower voltages and currents than typical EP methods to enhance tolerability while maintain successful transfection of the biomolecule (as evidenced the expression and subsequently immune response). The device is typically used with a pulse generator designed to deliver a constant voltage, current or a combination of both as desired. The electrical pulses used by the MIED to effect transfection of the cells in the skin tissue are any known pulse patterns that provides the low electrical energy required to yield the tolerable electroporation. In some embodiments, the MIED delivers an electric pulse to the desired tissue at voltage levels of 0.01 V to 70 V, 0.01 V to 50 V, 0.01V to 40 V, 0.01V to 30 V, 0.01V to 20 V, 0.01V to 15 V, 0.1 V to 70 V, 0.1 V to 50 V, 0.1V to 40 V, 0.1V to 30 V, 0.1V to 20 V, 0.1V to 15 V, and preferably 1V-15 V. More preferably the voltage levels are 15 V when adjacent electrodes of the MIED are spaced apart approximately 2 mm, and preferably 1.5 mm.

In some embodiments, the MIED delivers tolerable electrical energy that is characterized by an electrical pulse delivering the following current into the desired tissue: 0.2 mA to 100 mA, 0.1 mA to 100 mA, 0.5 mA to 100 mA, 1 mA to 100 mA, 1 mA to 80 mA, 1 mA to 60 mA, 1 mA to 50 mA, 1 mA to 40 mA, 1 mA to 30 mA, but preferably 1 mA to 100 mA, and more preferably 1 mA to 30 mA, and more preferably 10 mA.

The tolerable electrical pulses associated with the MIED will all be characterized by short duration of each pulse, including pulse lengths of from 5 msec to 250 msec, 10 msec to 250 msec pulse, 20 msec to 250 msec, 40 msec to 250 msec, 60 msec to 250 msec, 80 msec to 250 msec, 100 msec to 250 msec, 20 msec to 200 msec, 40 msec to 200 msec, 60 msec to 200 msec, 80 msec to 200 msec, 100 msec to 200 msec, 20 msec to 150 msec, 40 msec to 150 msec, 60 msec to 150 msec, 80 msec to 150 msec, 100 msec to 150 msec, 100 msec to 140 msec, 100 msec to 130 msec, 100 msec to 120 msec, 100 msec to 110 msec, and more preferably 100 msec.

The tolerable electric pulses associated with the MIED will also be characterized by low repeated pulses. The pulses delivered by the MIED are repeated to deliver the following number of pulses for each vaccination: 1, 2, 3, 4, 5, 6, 7, 8, 9, or 10, and preferably from 1-6 pulses, and more preferably 2 pulses.

Tissue for Administering Vaccine+EP

The MIED is for delivery of electroporation-enabling electrical energy to cells of skin tissue to aid the delivery of biomolecules to the cells therein, and preferably the vaccination with DNA vaccines. Preferably the electrodes penetrate only the skin tissue that is the live tissue layer just below the stratum corneum and above the basal layer; and preferably in the stratum granulosum layers only. The biomolecule is typically delivered to the target tissue using the Mantoux technique.

Battery Powered Version with Electronics in Handle (See FIG. 3)

The MIED can be a portable EP device. A portable self contained MIED device is provided wherein the device is hand-held and wherein the electric energy source for electric pulsing is at least one battery having a voltage potential of between 1.5 V and 12 V.

The portable MIED can comprise a housing within which is contained said battery, a circuit board comprising an electric circuit in electric communication with and powered by said battery, and at least one capacitor capable of holding a capacitance of between 1000 and 100000 uF (microFarads). In a related embodiment the components (i.e., battery, circuit, and capacitor) are generally spatially placed within said housing in a linear or side-by-side arrangement such that the housing can have a generally rectangular or cylindrical shape capable of being held in the hand of a person operating the device. For example, the housing will have a proximal end and a distal end such that the cylinder or long portion of said rectangle lies there between and wherein said battery is located within said proximal end of said housing and is accessible from such end via a removable cover. At the distal end of said housing can be located electrical conduits which are in electrical communication with said circuit and which serve as connectors for connecting to at least one cathode and at least one anode to be used in completing a circuit comprising an electroporative pulse powered by said battery through said capacitor and circuit. The distal end of said housing can also comprise in association with, or as part of, said housing a mechanism for attaching, semipermanently or permanently, and/or detaching same, a head assembly, said head assembly itself comprising any of a reservoir for containing a fluid therapeutic agent, an orifice in fluid communication with said reservoir through which said fluid can be directed to a body tissue, a source of energy for moving said fluid from said reservoir through said orifice, and at least one electrode comprising at least one anode and one cathode In some embodiments, the portable MIED is capable of delivering to skin tissue of a mammal an electric pulse capable of electroporating cells within said tissue, said electric pulse having a voltage generally of between 0.1 V and 70 V, preferably 0.1 V to 50 V, more preferably 1 V to 15 V. Further still, the device is capable of delivering an electroporating pulse of said field strengths for a time period of between 5 milliseconds and 250 milliseconds, and more typically of between 10 and 100 milliseconds, still more commonly between 30 and 70 milliseconds, and more preferably 50 milliseconds. Still further, the device is capable via its microprocessor of delivering either a bipolar pulse or a monopolar pulse of electroporating electric energy, which bipolar or monopolar pulses can comprise a predetermined train of multiple pulses, and/or voltage-shaped pulses, or even still exponentially discharging pulses. Such variable pulsing capability provides for the potential optimization of the electroporation process including optimization of the voltage, pulse shape, duration, and polarity of the electroporation pulses.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

A trial can be conducted to evaluate tolerability or the reduced pain generated by the electroporation devices described herein. Study personnel can start a stopwatch for each patient at the time of electroporation administration. Each patient will perform standard pain assessments under the supervision of trained study personnel, and they will record these assessments in a diary booklet at: five, 10, 15, 20, 30 and 45 minutes, one hour and one and one-half hours post-electroporation, then hourly through 12 hours post-electroporation, and at 16 hours and 24 hours post-electroporation. Patients measured pain intensity using both a categorical scale and a VAS. As previously stated the categorical scale included four categories:

0=none, 1=mild, 2=moderate and 3=severe.

The VAS is a 100-mm—long horizontal line on which 0 mm indicated no pain and 100 mm indicated worst pain. Using this 100 mm scale, a near painless score would be a score that is within 20 mm from a score that indicate pain free (no pain felt). In some cases near painless will be scores of 10 mm from a pain free score.

Methods

The following methods are utilized in each of the examples, below, where appropriate per discussion.

Minimally Invasive Device Design—Electrode arrays consisting of a 4×4 gold plated trocar needle of 0.0175 inch diameter at a 1.5 mm spacing were constructed to be used in conjunction either with the ELGEN1000 (Inovio Pharmaceuticals, Inc., Blue Bell, Pa.) pulse generator or a battery powered low voltage circuit.

Plasmid Preparation—The gWiz GFP plasmid were purchased from Aldevron (Fargo N.Dak.). The NP plasmid encodes the full length NP derived from Puerto Rico 8 (H1N1) strain of influenza. The M2 plasmid encodes the full length M2 derived from New Caledonia/99 (H1N1) strain of influenza. The construct had the nucleus targeting signals mutated and was optimized and synthesized by GeneArt (Germany). All plasmids were diluted in 1×PBS prior to injection. SYNCON™ (Synthetic DNA Construct) influenza vaccine plasmid cocktail (100 µg/plasmid) containing pGX2005 (SYNCON™ vaccine construct that encodes a consensus sequence of H1HA) and pGX2009 (SYNCON™ vaccine construct that encodes a consensus sequence of swine H1HA) were diluted in 1×PBS prior to injection.

Animals—Female Hartley guinea pigs (strain code 051), female New Zealand rabbits and female Balb C mice were purchased from Charles River Laboratories. Female Wistar rats were purchased from Charles River Laboratories. Female Yorkshire pigs were purchased from S & S Farm's (Ramona, Calif.). Guinea pigs, rats, rabbits and mice were housed at BioQuant (San Diego, Calif.). Male (4) and female (4) macaques (Macaca mulatto) were individually housed at BIOQUAL, Inc. (Rockville, Md.), with ad libitum access to food and water. Macaques were allowed to acclimate for at least 30 days in quarantine prior to experimentation. All animals were housed and handled according to the standards of the Institutional Animal Care and Use Committee (IACUC).

Preparation of Animals—The GFP reporter results observed on the Hartley guinea pigs after hair removal was the same as the results observed on the IAF hairless guinea pigs in previous experiments. Since hair removal appeared to have no effect on the resulting transfection and due to cost considerations, we chose to carry out the rest of the study in the Hartley animals. Hartley guinea pigs were shaved and stubble removed by dilapatory cream (Veet) 24 h prior to treatment. Mice, rats, rabbits, pigs and macaques were shaved prior to treatment.

DNA Injections—Macaques were sedated with injected ketamine. All other animals were sedated with inhaled isoflurane. All animals were injected intradermally (Mantoux method—29 gauge Insulin needle) with 50 µl of 1×PBS containing the desired dose of plasmid. Mice were injected intramuscularly into the quadriceps with 50 µl of 1×PBS containing the desired dose of plasmid. Macaques were injected with intramuscularly into the quadriceps with 400 µl of 1×PBS containing the desired dose of plasmid. Empty vector was added to maintain equal DNA amounts for each group.

Dermal Device Electroporation—Immediately following injection of DNA, the dermal device was applied to the site of dermal injection. The array was "wiggled" at the injection site to ensure good contact and electrotransfer achieved through pulse generation either from the Elgen 1000 or a low voltage battery circuit. The parameters used were three 15 volt pulses of 100 ms duration.

Muscle Electroporation—Immediately following IM injection, electroporation was performed by inserting a 27 G, 2 needle array with a 4 mm electrode spacing at the site of the injected muscle. Two 125 V/cm pulses lasting 60 ms each were delivered using the Elgen 1000.

Imaging of Skin—Skin samples or biopsies were removed post-mortem from animals after termination and stored on ice until imaged under an OV 100 imaging microscope (Anti Cancer Inc., San Diego, Calif.) at 480 nm.

Histopathology—Skin samples or biopsies were removed post-mortem from animals after termination and immediately preserved in 10% neutral buffered formalin and sent to Pacific Pathology, San Diego, Calif., for processing and histopathological analysis. Appropriate tissues were trimmed, processed, embedded in paraffin, sectioned at approximately 5 µm, and stained with hematoxylin and eosin. The resulting slides were examined by a board certified pathologist. The sections were visualized using a Zeiss Axioplan microscope with a 10× objective at the Burnham Institute, San Diego, Calif.

Detection of NP antibodies in immunized mouse sera—Antibody responses against NP were evaluated by ELISA using serum from immunized mice. Mice were bled retro-orbital two weeks after last immunization. Nunc Maxi-Sorp Immuno Plates were coated NP (5 µg/mL, Imgenex IMR-274) at 4° C. overnight. Unbound antigens were washed off the plate by an automatic plate wash using PBS with 0.05% Tween-20. The plates were blocked for non-specific binding by adding 200 uL of PBS with 0.5% BSA for one hour at 37° C. After washing as above, serum was diluted 1:50 in PBS with 0.2% BSA and 0.05% Tween-20 and added to the first well. A serial dilution was done by diluting 1:3 to 1:5 for every well. The serum was incubated for two hours at 37° C. before washing. Anti-mouse IgG-biotin (B9904-5 ml; Sigma-Aldrich, St Louis, Mo., USA) was diluted 1:10000 and 50 µL is added to each well and incubate one hour at 37° C. before washing. This was followed by adding 50 µL streptavidin-HRP (Southern Biotech, Birmingham, Ala., USA) diluted 1:1000 to each well and incubate one hour at 37° C. before washing. The final step was done by adding 50 µL HRP substrate (P-9187, Sigma-Aldrich) and incubating at room temperature in the dark for 10 minutes before reading the optical density (OD) at 450 nm. A reading was considered positive if the OD was three times higher than the OD from naïve mice serum. Results were presented as end-point titer, i.e. the last dilution where the OD was more or equal to three times higher than the naïve serum.

ELISpot Assay—Two weeks after the immunization, splenocytes from each group of mice were isolated. Single cell suspensions were cleared of red blood cells using RBC lysis buffer (eBioscience). The ELISPOT assay kit was purchased from R&D Systems. 96-well ELISPOT plates (Millipore) were coated with anti-mouse interferon (IFN)-γ monoclonal antibody. After overnight incubation at 4° C., the wells were washed and blocked with blocking buffer according to the protocol from R&D Systems. Pooled splenocytes from each group were added to the wells and incubated with 1 µg/mL NP 147 (TYQRTRALV Biosynthesis Inc.) for 48 h. The plates were then washed and developed following the protocol described as manufacturer. The spots were counted and analyzed by Cellular Technology Ltd.

Intranasal Influenza Challenge—Balb/c mice in groups of 10 were immunized on week 0, 3, and 6. Mice were immunized: Prime 30+30 ug Week 0, Boost 30+30 ug Week 3, Boost 100+100 ug Week 10. At week 12, Flu challenge experiments were conducted using BSL IV protocols at The National Microbiology Laboratory, Public Health Agency of Canada, Winnipeg, MB, Canada according to ethical guidelines of their ethical committee. A 100×LD50 dose of H5N1 ANietnam/1203/04 strain was used for nasal challenge. Mice were then monitored for survival and body-weight every day for 21 days following challenge.

HAI Assays—Animals were bled and sera samples immediately stored on dry-ice before being shipped to BIOQUAL, Rockville, Md. for processing. Sera was treated with receptor-destroying enzyme by diluting 1 part serum with 3 parts enzyme and were incubated overnight at 37° C. water bath. The enzyme was inactivated by 30-min incubation at 56° C., followed by the addition of 6 parts phosphate-buffered saline for a final dilution of/1;10. HAI assays were performed in V-bottomed 96-well microtiter plates, using 4 hemagglutination units of virus and 1% red blood cells as previously described. Virus used for the HAI assays are obtained from the influenza branch of the CDC.

Example 1

Electroporation Using a Minimally-Invasive Device Results in Robust Reporter Gene Transfection A minimally-invasive electrode device (MIED) was designed for use with DNA vaccine delivery. This new applicator consists of gold-plated stainless steel needle electrodes with trocar grinds (the electrodes have a tip on the distal end that is blunt with a sharp point) at 1.5 mm spacing in a 4×4 array pattern (FIGS. 4*a* and 4*c*). Alternating rows of four electrodes can be fired with reverse polarity: positive than negative. The electrodes are captured in electrical sockets within the plastic handle, allowing each electrode to be addressed individually for alternative firing patterns. The device is designed to only make contact with the surface of the skin and not directly penetrate the tissue. Upon proper contact, the sharpness of the electrodes can allow the device array to disrupt the stratum corneum barrier layer, assuring consistent impedance measurements resulting in repeatable electroporation treatments. The prototype device was built with attachment cord for linkage to pulse generator (FIG. 4*b*).

The lower limits of voltage parameters required for successful transfection and immune responses using this new minimally-invasive, needle electrode device (MIED) were studied. Separate skin sites on the flank of a guinea pig were injected using the Mantoux technique with 50 μl of 1 mg/ml GFP plasmid and immediately pulsed using the MIED set at as low a voltage as 15 V (FIG. 5*a*). Robust and reproducible GFP transfection was visible 8 hours following treatment but peaked at 3 days. Minimal or no GFP transfection was detectible following GFP plasmid injection alone (data not shown). While a range of electrical parameters and voltages resulted in GFP transfection, pulses at 15 volts were more reproducible (data not shown). Reproducibility was quantified and assessed by positive pixel count following fluorescence microscopy at standardized conditions. The most consistent pixel count numbers within a defined area were obtained at the 10-15 volt parameters. Actual GFP transfection patterns appeared as distinct "islands" around the contact point with each electrode (FIG. 5*b*). Effective EP is shallow and highly localized about electrode tip at low voltage, thus, no meaningful transfection below the stratum basale layers of the epidermis.

To ensure that the robust transfection was not a guinea pig specific phenomenon, GFP localization was carried out in a range of species. Skin sites on mice, rabbits, rats and pigs were injected with 50 μl (30 μl in mice) of 1 mg/ml GFP plasmid and immediately pulsed using MIED. All species demonstrated robust dermal GFP transfection following electroporation with minimal or no transfection detected following GFP plasmid injection alone (FIG. 6). In all species, strong GFP positivity was detected in all electroporated skin samples. However, only the rabbit samples demonstrated the distinctive "island" pattern observed in the guinea pig samples (FIG. 5). The GFP localization on the rat, mouse and pig skin appeared more diffuse. The actual transfected area was similar between rat, rabbit and pig (approximately 4 $mm^2$) since that was a function of the injection bubble size. The transfected area on mouse skin was slightly smaller due to the smaller injection volume. On the mouse panel, the entire skin of the mouse is shown so that relative size can be appreciated. GFP positive cells were detected only on the surface of the skin in the rat, rabbit and pig samples. No GFP signal was observed on the underside of these samples. The underside of the mouse skins did appear to have a positive GFP signal. However, this appears to be related to the thinness of the skin sample.

This data suggests that the MIED can efficiently transfer plasmid to skin across both small and large animal models.

Example 2

Electroporation Using a Minimally-Invasive Device—Histological Analysis Demonstrates Transfection in the Upper Layers of the Epidermis To address the effect of electroporation by the MIED on a cellular level, histological analysis was carried out. Sites on a guinea pig were injected with 50 ul of 1 mg/ml GFP plasmid and immediately pulsed using the MIED. Biopsy samples were removed 3 days post treatment, fixed, paraffin sectioned and H&E stained (Slide not shown). Pathological analysis revealed no associated tissue damage following electroporation with the minimally-invasive device. High powered microscopy revealed that the majority of GFP transfection occurred in the stratum granulosum cell layer of the epidermis (Slide not shown). GFP positive cells were also detected in the stratum basale. In contrast, only a few GFP positive cells were detected in the biopsy that received GFP plasmid injection alone. This was in direct contrast to the robust signal observed in the biopsy sample from tissue that had received electroporation. A visual estimation of enhancement of expression would be in excess of 100-1000 fold based on number of GFP positive cells relative to DNA alone.

Example 3

Electroporation Using a Minimally-Invasive Device—Results in Robust Cellular Responses and Provides 100% Protection Against Lethal Challenge in Mice Mice were immunized with DNA encoding for NP and M2 influenza antigens: Prime 30+30 ug Week 0, Boost 30+30 ug Week 3, Boost 100+100 ug Week 10. Matched NP antigen from Puerto Rico/39 strain and matched M2 antigen from New Caledonia/99 strain were optimized, synthesized and then cloned into the backbone of a clinically approved mammalian expression vector, pMB76.5. The NP and M2e antigens were chosen to assess predominantly cellular immunity. These proteins are not able to induce neutralizing antibody responses.

Groups of mice were electroporated either with the minimally-invasive dermal device or with the Elgen 1000 intramuscular device (Inovio Pharmaceuticals, Inc., Blue Bell, Pa.). Induction of potent cellular and humoral responses in the mouse model as measured by antigen specific T-cell ELISPot assays and antibody titers were observed in all mice. Antigen specific CTL responses were 200+/−57.9 SFU/10^6 splenocytes against NP for MIED and 85+/−36.3 SFU/10^6 splenocytes against NP for IM (FIG. 7A). Those animals electroporated intradermally showed higher titers and cellular responses although not statistically significant.

In a bid to determine if the induced immune responses were capable of impacting infection, mice were challenged with a lethal dose of influenza A/H5N1Nietnam/1203/04 via intranasal (i.n.) inoculation (FIG. 7B). The VN/1203/04 (H5N1) strain of influenza is known to cause rapid morbidity and mortality. While 100% of the naïve mice succumbed to infection by day 11, 100% of the mice immunized with the MIED were protected against both morbidity and mortality through day 15 (end of the experiment). Similarly, at day 15, 90% of the IM immunized positive control animals survived.

Example 4

Electroporation Using a Minimally-Invasive Device Results in Humoral Immunogenicity and Protective HI Titers
Guinea Pigs It is difficult to target the dermis in mice because of the extremely thin skin structure and the close proximity of underlying muscle. For this reason, often immune responses induced in mice are a combination of skin and muscle. Therefore, the MIED was tested in a larger animal model-guinea pigs, which have a better defined skin structure.

Guinea pigs were immunized with a previously described consensus SYNCON™ influenza vaccine by intradermal electroporation via MIED. Animals were vaccinated with a vaccine plasmid cocktail (100 μg/plasmid) containing pGX2005 (SYNCON™ vaccine construct that encodes a consensus sequence of H1HA) and pGX2009 (SYNCON™ vaccine construct that encodes a consensus sequence of swine H1HA) in a volume of 50 μl diluted in 1×PBS. Two weeks following two immunizations, each animal developed robust HAI titers over 1:40 against H1N1 the pandemic Mexico/2009 strain, and also to A/H3N2 Brisbane strain, and to an extent the A/H5N1 Vietnam/2005 strain (FIG. 8).
Macaques Macaques were vaccinated with a previously described consensus influenza vaccine plasmid cocktail (100 μg/plasmid) containing pGX2005 (SYNCON™ vaccine construct that encodes a consensus sequence of H1HA) and pGX2009 (SYNCON™ vaccine construct that encodes a consensus sequence of swine H1HA) in a volume of 50 μl by either intradermal (MIED) or intramuscular electroporation (Elgen 1000). Following two immunizations, four out of four animals developed HAI titers over 1:40 against the H1N1/Mexico/2009 strain, and against the A/H1N1/New Caledonia strain, when immunized intradermally with MIED (FIG. 9).

Example 5

Tolerability Study with the Minimally-Invasive Device

To assess the pain level of EP with the minimally invasive EP device is applied to the epidermal layers between the stratum corneum and the basal layer. The visual response of testing with anestitized animals does not produce the muscle twitching seen with higher power pulses or invasive electrode arrays, while demonstrating effective transfection with reporter genes and immune response with antigenic plasmids. Pulse voltages up to 15V and currents up to approximately 30 mA produce only a mild sensation, while inducing protective immune responses in guinea pigs and rhesus macaque monkeys for influenza.

In vivo EP is applied using the invasive dermal device array has shown marked reduction in pain compared with intramuscular device, invasive arrays. It is expected that the MIED results even greater reduction in pain.

In vivo EP is applied using the MIED array following an ID injection of 0.9% saline into the stratum granulosum. Patients are injected with 0.15 mL saline in stratum granulosum layer and then EP is performed using CELLECTRA® 2000 (Adaptive Constant Current Device or, alternatively, an Elgen 1000 device, Inovio Pharmaceuticals, Inc., Blue Bell, Pa.). EP parameters are 15 V, 100 msec pulse, and 3 pulses in total.

For each subject, the injection site pain would be assessed by using a Visual Analog Score (VAS), which is determined immediately after EP.

What is claimed is:

1. An electroporation device capable of delivering to a subject a tolerable electrical potential to layers of epidermal tissue between stratum corneum and basal layers that results in electroporation of cells in said epidermal tissue, comprising:

a voltage generator; and
an array having a plurality of needle electrodes in electrical communication with the voltage generator;
wherein each one of the plurality of needle electrodes is spaced apart from each adjacent needle electrode at a spacing distance of about 0.5 mm to about 2.5 mm;
wherein the voltage generator delivers via the plurality of needle electrodes an electrical potential of about 0.1 volts to about 70 volts to the epidermal tissue; and
wherein each of the plurality of needle electrodes defines a central axis and a distal end, wherein the distal end defines a trocar tip having a sharp point and a plurality of planar surfaces that extend distally to the sharp point, wherein the plurality of planar surfaces are oriented, respectively, at generally blunt angles between 10 degrees from the central axis and substantially perpendicular to the central axis, and
wherein the generally blunt angles and the sharp point of the trocar tip of each needle electrode and the spacing distance collectively allow the plurality of needle electrodes to 1) penetrate the layers of the epidermal tissue between stratum corneum and basal layers at depths of 0.1 mm or less, and 2) deliver the electrical potential from the voltage generator to the layers of epidermal tissue between stratum corneum and basal layers such that at least a majority of the electroporation of cells occurs in cells of stratum granulosum.

2. The electroporation device of claim 1, wherein the plurality of needle electrodes deliver a tolerable electrical potential to the cells of the epidermal tissue that is near painless as measured by a visual analog scale.

3. The electroporation device of claim 1, wherein the plurality of needle electrodes are adapted to penetrate the epidermal tissue at depths of from about 0.01 mm to about 0.04 mm.

4. The electroporation device of claim 1, wherein the spacing distance is about 1.5 mm.

5. The electroporation device of claim 1, wherein the voltage generator delivers to the epidermal tissue an electrical potential of about 1 volt to about 15 volts.

6. The electroporation device of claim 1, wherein the voltage generator delivers to the epidermal tissue an electrical potential at a current ranging from about 1 mA to about 50 mA.

7. The electroporation device of claim 1, wherein the voltage generator delivers to the epidermal tissue an electrical potential for a duration ranging from about 5 msec to about 250 msec.

8. The electroporation device of claim 1, wherein the plurality of needle electrodes deliver the electrical potential to the layers of the epidermal tissue between stratum corneum and basal layers in a manner that results in no visible tissue damage per a histopathology analysis of the tissue.

9. The electroporation device of claim 1, wherein each of the plurality of needle electrodes comprises stainless steel and is gold-plated.

10. The electroporation device of claim 9, wherein the plurality of planar surfaces consists of three planar surfaces.

11. A tolerable method of delivering a biomolecule to cells of epidermal tissue of a subject by electroporation-assisted delivery using the electroporation device of claim 1, the method comprising:
   administering the biomolecule to the cells;
   contacting the plurality of needle electrodes to the epidermal tissue so that the sharp points of the plurality of needle electrodes penetrate through the stratum corneum and reside in layers above the basal layers; and
   delivering a tolerable electrical potential from the voltage generator to the cells of the epidermal layer via the plurality of needle electrodes.

12. The method of claim 11, wherein the contacting step comprises manipulating the plurality of needle electrodes to penetrate the epidermal tissue at depths of 0.1 mm or less.

13. The method of claim 11, wherein the contacting step comprises manipulating the plurality of needle electrodes to penetrate the epidermal tissue at depths of from about 0.01 mm to about 0.04 mm.

14. The method of claim 11, wherein the delivering step comprises delivering a tolerable electrical potential that generates a pain assessment by said subject that is near painless as measured by a visual analog scale.

15. The method of claim 11, wherein the delivering step comprises delivering an electrical potential of about 0.1 volts to about 15 volts to the cells.

16. The method claim 11, wherein the delivering step comprises delivering an electrical potential at a current ranging from about 1 mA to about 50 mA to the cells.

17. The method of claim 11, wherein the delivering step comprises delivering an electrical potential for a duration ranging from about 5 msec to about 250 msec.

18. An electroporation device capable of delivering to a subject a tolerable electrical potential to layers of epidermal tissue between stratum corneum and basal layers that results in electroporation of cells in said tissue, comprising:
   a portable housing configured for hand-held operation;
   a voltage generator contained in the portable housing; an array housing carrying a plurality of needle electrodes; and
   an electrode housing coupled to the array housing, wherein the electrode housing has a plurality of electrical sockets, the plurality of needle electrodes are received within the plurality of electrical sockets, the plurality of electrical sockets place the plurality of needle electrodes in electrical communication with the voltage generator, and the array housing is attachable to and detachable from the portable housing;
   wherein each one of the plurality of needle electrodes is spaced apart from each adjacent needle electrode at a spacing distance of about 0.5 mm to about 2.5 mm;
   wherein the voltage generator delivers via the plurality of needle electrodes an electrical potential of about 0.1 volts to about 70 volts to the epidermal tissue; and
   wherein the plurality of needle electrodes extends distally from the array housing, and the plurality of needle electrodes each have a distal end that defines a trocar tip having a sharp point and a plurality of planar surfaces that extend distally to the sharp point, wherein the plurality of planar surfaces are oriented, respectively, at generally blunt angles, wherein the generally blunt angles and the sharp point of each needle electrode and the spacing distance collectively allow the plurality of needle electrodes to 1) penetrate the layers of the epidermal tissue between stratum corneum and basal layers at depths of 0.1 mm or less while avoiding penetration into the basal layers, and 2) deliver the electrical potential from the voltage generator to the layers of the epidermal tissue between stratum corneum and basal layers such that at least a majority of the electroporation of cells occurs in cells of stratum granulosum.

19. The electroporation device of claim 18, wherein the voltage generator comprises at least one battery.

20. The electroporation device of claim 19, wherein the portable housing further comprises:
   a circuit board having an electric circuit that is in electrical communication with the at least one battery and is powered by the at least one battery; and
   at least one capacitor in electrical communication with the electric circuit,
   wherein the battery provides the electrical potential to the plurality of needle electrodes through the at least one capacitor and the electric circuit.

* * * * *